United States Patent [19]

Loh et al.

[11] Patent Number: 5,008,435
[45] Date of Patent: Apr. 16, 1991

[54] PREPARATION OF URETHANES

[75] Inventors: Kuo-Liang Loh; Puh Shieh, both of Hsinchu; Y. S. Chao, Kao-Hsiung; Tsu-Kung Chuang, Hsinchu, all of China

[73] Assignee: Industrial Technology Research Institute, Taiwan

[21] Appl. No.: 275,261

[22] Filed: Nov. 22, 1988

[51] Int. Cl.$^5$ ............................................. C07C 261/00
[52] U.S. Cl. ........................................ 560/24; 560/25; 560/26; 560/28; 560/32; 560/115; 560/132; 560/134; 560/157; 560/158; 560/163; 560/164; 560/166
[58] Field of Search ................... 560/24, 25, 26, 28, 560/32, 115, 132, 134, 157, 158, 163, 164, 166

[56] References Cited

U.S. PATENT DOCUMENTS

| | | | |
|---|---|---|---|
| 3,338,956 | 8/1967 | Mountfield et al. | 260/471 |
| 3,454,620 | 7/1969 | Gamlen et al. | 560/24 |
| 3,993,685 | 11/1976 | Zajacek et al. | 260/471 |
| 4,603,216 | 7/1986 | Grate et al. | 560/24 |

FOREIGN PATENT DOCUMENTS 0083096 6/1983 European Pat. Off. .

Primary Examiner—Bruce Gray
Attorney, Agent, or Firm—Darby & Darby

[57] ABSTRACT

Process for producing urethanes, by reacting an organic hydroxyl group containing compound and carbon monoxide, either (i) with an organic nitro group containing compound, e.g. nitrobenzene, or (ii) with a primary amine, e.g. aniline, and oxygen, the reacting in both cases being carried out in the presence of a non-noble metal catalyst system comprising a copper catalyst, preferably mixed with a promoter such as a nitrogen or phosphorous containing organic compound for the (i) nitro compound reaction, or an alkali salt for the (ii) amine reaction, e.g. at 200–8000 psig and 100°–300° C., using 0.05–0.4 mole copper catalyst and 0.01–10 moles promoter per mole (i) nitro compound or (ii) amine, and 2–500 moles carbon monoxide, and (in the case of the (ii) amine) 0.5–5 moles oxygen, per mole of the (i) nitro compound or (ii) amine.

14 Claims, No Drawings

PREPARATION OF URETHANES

FIELD AND BACKGROUND OF THE INVENTION

Urethanes can be catalytically or thermally decomposed to form corresponding isocyanates, which are important key materials in the polyurethane (PU) industry as well as in the pharmaceutical industry. In the prior art, there are two major methods disclosed by various patents for urethane preparation.

One method is reductive carbonylation, which can be represented by the following general reaction equation:

$$R(NO_2)_x + 3xCO + xR'OH \rightarrow R(NHCOOR')_x + 2xCO_2 \qquad (I)$$

Another method is oxidative carbonylation, which can be represented by the following general reaction equation:

$$R(NH_2)_x + xCO + xR'OH + x/2O_2 \rightarrow R(NHCOOR')_x + xH_2O \qquad (II)$$

In these formulas, R is the organic radical of the corresponding nitro or primary amino group containing compound, R' is the organic radical of the hydroxyl group containing compound, and x is an integer.

The disclosed catalyst systems for both methods mainly are group VIIIB metals of the periodic table, in combination with nitrogen or phosphorous containing compounds as promoters.

For the reductive carbonylation method, U.S. Pat. No. 4,603,216 discloses that a halide-free ruthenium complex catalyst comprising a bis-phosphine ligand was employed to catalyze the reaction. Also, U.S. Pat. No. 3,338,956 describes a process for the manufacture of urethanes at high temperature and high pressure in the presence of a metal carbonyl of elements in groups VIB, VIIB and VIIIB of the periodic table, while U.S. Pat. No. 3,998,685 describes a process where palladium halides and ferric chloride were used. See, also: S. Oenini, et al, J. Chem. Soc., Chem. Commun., 1286, 1984, in which ruthenium carbonyl catalyst was used to prepare urethanes with high selectivity in the presence of alkyl ammonium salt; and Y. Watanabe, et al, Bull. Chem. Soc. Jpn., 56: 3343, 1983, which demonstrated that a series of nitroarenes was transformed into corresponding urethanes in moderate to excellent yields with a platinum complex as catalyst.

For the oxidative carbonylation method, U.S. Pat. No. 4,297,501 discloses a catalyst system where halides of a noble metal of the VIIIB group of the periodic table, and a compound capable of undergoing redox reactions were employed. Also, European Pat. Appl. 083096 (published 1983) discloses a process for preparing urethane in the presence of a catalyst system comprising the Pt group metals and halides of alkali metals or alkaline earth metals.

Of course, the fact that the above mentioned patent teachings use expensive noble metal catalysts diminishes the commercial attractiveness of these known processes.

DESCRIPTION OF THE INVENTION

This invention relates to a process for preparing urethanes, either (i) by the method of reacting an organic hydroxyl group containing compound and carbon monoxide with an organic nitro group containing compound, or (ii) by the method of reacting an organic hydroxyl group containing compound and carbon monoxide with a primary amine and oxygen, i.e. molecular oxygen, in each case in the presence of a non-noble metal catalyst system.

The process of this invention which involves the reaction of the organic hydroxyl group containing compound and carbon monoxide with the organic nitro group containing compound is effected in accordance with the known reductive carbonylation reaction mechanism per equation (I) above.

Analogously, the process of this invention which involves the reaction of the organic hydroxyl group containing compound and carbon monoxide with the primary amine and oxygen is effected in accordance with the known oxidative carbonylation reaction mechanism per equation (II) above.

Both such methods according to this invention utilize a copper catalyst as the non-noble metal catalyst system for the particular reaction, preferably a mixture of a copper catalyst with one or more nitrogen and/or phosphorous containing organic compounds as promoter for the reductive carbonylation, or with one or more alkali salts as promoter for the oxidative carbonylation. In each of the two methods, high selectivity for urethane can be appropriately achieved at significant conversion levels of the starting nitro group containing compound or primary amine.

In essence, this invention advantageously provides a process using a relatively inexpensive, yet highly active, copper based catalyst system, e.g. especially in high concentration (>10 mol %), for efficient production of urethanes, or carbamates, in high yields, e.g. desirably on the order of 90% conversion and above, and 90% urethane selectivity and above, especially at high pressure, e.g. about 1000 psig, and does not require phosgene.

For the reductive carbonylation method according to this invention, suitable nitro group containing compounds, or nitro compounds, which may be used include organic compounds containing at least one nitro group, as represented by the following general formula:

$$R(NO_2)_x$$

wherein R is an aliphatic group consisting of 1 to 20 carbon atoms, such as alkyl and cycloalkyl, which may be substituted with one or more aromatic groups such as phenyl, naphthyl, and the like; or an aromatic group consisting of 6 to 20 carbon atoms, e.g. including 6 to 10 ring carbon atoms, such as phenyl, naphthyl, and the like, which may be substituted with one or more aliphatic groups such as alkyl groups; and x is an integer of from 1 to 3.

Exemplary nitro compounds of the above type include aliphatic nitro compounds such as nitromethane, nitroethane, nitrobutane, nitrocyclopentane, nitrooctadecane, phenylnitromethane, dinitroethane, dinitrohexane, and the like, and aromatic nitro compounds such as nitrobenzene, 2,4- and 2,6-dinitrotoluene, and the like.

For the oxidative carbonylation method according to this invention, suitable primary amines which may be used include organic compounds containing at least one primary amino group, as represented by the following general formula:

$$R(NH_2)_x$$

wherein R and x are the same as defined above.

Exemplary primary amines of the above type include aliphatic amines such as methylamine, ethylamine, hexylamine, dodecylamine, ethylenediamine, 1,2,3-triaminopropane, triaminododecane, and the like, and aromatic amines such as aniline, 2,6-diaminotoluene, diaminonaphthalene, and the like.

Suitable organic hydroxyl group containing compounds, or alcohols, which may be used for both the reductive carbonylation method and the oxidative carbonylation method according to this invention, include those which contain at least one aliphatic alcoholically bound hydroxyl group, or at least one phenolically bound hydroxyl group, as represented by the following general formula:

$$R'(OH)_x$$

wherein R' is the same as defined above for R, i.e. an aliphatic group consisting of 1 to 20 carbon atoms, such as alkyl and cycloalkyl, which may be substituted with one or more aromatic groups such as phenyl, naphthyl, and the like; or an aromatic group consisting of 6 to 20 carbon atoms, e.g. including 6 to 10 ring carbon atoms, such as phenyl, naphthyl, and the like, which may be substituted with one or more aliphatic groups such as alkyl groups; and x is the same as defined above.

Exemplary alcohols of the above type include aliphatic alcohols such as methanol, ethanol, n-propanol, isopropanol, pentanol, benzyl alcohol, ethylene glycol, glycerol, hexane triol, and the like, and aromatic alcohols such as phenols, naphthols, and the like.

Aliphatic alcohols, as distinguished from aromatic alcohols such as phenols and naphthols, are the preferred hydroxyl group containing compounds. In particular, higher urethane yields are achieved using higher carbon chain aliphatic alcohols such as isopropanol and pentanol.

The non-noble metal catalyst system used in the process of this invention is generally a homogeneous copper containing catalyst, such as a copper catalyst alone, i.e. unpromoted copper catalyst, or preferably a mixture of a copper catalyst with a promoter, the promoter being at least one nitrogen or phosphorous containing organic compound for the reductive carbonylation, or at least one alkali salt for the oxidative carbonylation.

Suitable copper catalysts include metallic copper as well as organic and inorganic copper (II, i.e. cupric) salts, such as pure copper powder, and copper (i.e. cupric) halides, acetates and nitrates, the copper halides being preferred. Besides copper powder, exemplary homogeneous copper catalysts include cupric salts such as cupric chloride, cupric iodide, cupric bromide and copper (II) acetate.

Suitable nitrogen containing compounds which may be used as promoter for the reductive carbonylation include tertiary amines and quaternary ammonium salts.

Representative tertiary amines include aliphatic tertiary amines, e.g. trialkylamines, such as triethylamine, and the like, aromatic tertiary amines, e.g. phenylamines, which may be substituted with one or more aliphatic groups, e.g. alkyl groups, such as N,N-dimethyl aniline, and the like, and heteroaromatic or N-heterocyclic tertiary amines, such as pyridine, quinoline, indole, pyrazine, and the like.

Representative quaternary ammonium salts include aliphatic quaternary ammonium halides, e.g. tetraalkylammonium halides, and in particular iodides and bromides, such as tetramethylammonium iodide, tetramethylammonium bromide, tetra-n-butylammonium iodide, tetra-n-butylammonium bromide, and the like.

Suitable phosphorous containing compounds which may be used as promoter for the reductive carbonylation include organophosphines, and in particular tertiary phosphines, e.g. tertiary aromatic and/or aliphatic phosphines, especially triaromatic phosphines such as triphenylphosphine, and the like, and trialkylphosphines such as tripropylphosphine, tributylphosphine, and the like.

These nitrogen or phosphorous containing organic compounds may be used alone or in admixture, e.g. in a molar ratio of about 0.1–10:1, preferably about 1:1, as promoter for the reductive carbonylation.

Suitable alkali salts which may be used as promoter for the oxidative carbonylation include alkali metal salts, in particular alkali metal halides, such as lithium iodide, sodium iodide, potassium iodide, cesium iodide, lithium bromide sodium bromide, rubidium bromide, potassium bromide, cesium bromide, and the like.

These alkali salts may be used alone or in admixture, e.g. in a molar ratio of about 0.1–10:1, preferably about 1:1, as promoter for the oxidative carbonylation.

The process of this invention can be carried out in the absence of a solvent. However, an inert organic solvent can be used if necessary or desired, such as benzene, chlorobenzene, xylene, and the like.

The amount of the non-noble metal catalyst employed in the reaction is generally equivalent to about 0.05 to 0.40 mole of copper catalyst, as copper (i.e. cupric) compound (moles) or copper powder (gram atoms), and where used in admixture with a promoter, then also about 0.01 to 10 moles of the promoter, per mole of the nitro group containing compound or primary amine used. The median of each of these two ranges is preferred, but the particular range used will generally depend on the equipment and specific conditions employed, i.e. temperature, pressure, extent of agitation or mixing of the reactants, and the like.

Exemplary preferred ranges are about 0.1–0.3 mole copper catalyst, and about 0.02–10, especially about 0.02–1, or even about 0.05–10, moles promoter, per mole of nitro group containing compound or primary amine used.

Desirably, the molar ratio of promoter to copper catalyst is about 0.2–25:1, and preferably about 1–5:1.

In the case of both the reductive carbonylation and oxidative carbonylation, although a molar excess of the organic hydroxyl group containing compound, such as an aliphatic alcohol, is normally used, e.g. about 5–30, especially about 10–25, moles alcohol per mole of nitro group containing compound or primary amine, nevertheless an equivalent amount of such hydroxyl group containing compound can be utilized, if desired, for each equivalent of nitro group containing compound or primary amine employed.

The amount of carbon monoxide used in the process of this invention, both for the reductive carbonylation and the oxidative carbonylation, is generally about 2 to 500, preferably about 10–200, moles per mole of nitro group containing compound or primary amine used, or ideally for each mole of urethane to be produced.

For the oxidative carbonylation, about 0.5 to 5 moles of oxygen are used per mole of primary amine used, or ideally for each mole of urethane to be produced.

For both the reductive carbonylation method and the oxidative carbonylation method according to this invention, the process is generally carried out at a pressure of about 200 to 8000 psig, preferably at about 400-2000 psig, and at a temperature of about 100° to 300° C. preferably at about 125°-200° C. The reaction time is usually about ¼ to 8 hours, depending on the reaction pressure and temperature selected.

For both the reductive carbonylation method and the oxidative carbonylation method, the hydroxyl group containing compound, nitro group containing compound or primary amine, and unpromoted copper catalyst, or copper catalyst and associated promoter, are typically admixed in a pressure reactor, optionally with an inert solvent, and the reactor then pressurized with carbon monoxide, or with carbon monoxide and oxygen, as the case may be, at room temperature, followed by heating with mixing agitation for the required reaction time, after which the reactor is cooled, and the reaction mixture recovered and worked up in the usual way.

The following examples are merely illustrative of preferred embodiments of the invention. Many variations thereon may be made without departing from the spirit of the disclosed invention, as will be evident to those skilled in the art, and such variations are intended to come within the scope of what is claimed.

Reductive Carbonylation Process

EXAMPLES 1-6

A mixture containing 0.62 g (5.0 mmol) nitrobenzene, 0.085 g (0.5 mmol) CuCl$_2$.2H$_2$O, 5.0 ml (86 mmol) ethanol and 0.1 mmol of the various promoters as listed in table I below (the Example 4 promoters being in 1:1 molar ratio), were introduced into a 125 ml autoclave. The autoclave was then pressurized with carbon monoxide to 1,000 psig at room temperature, after which the mixture was heated to 180° C. and stirred for 4 hours. Upon cooling to room temperature, the autoclave was vented and flushed with nitrogen. The mixture was discharged, filtered and analyzed by gas chromatography.

The results are shown in table I, the selectivity indicated being based on nitrobenzene. Examples 2 to 4 show that while aniline selectivity was enhanced using triphenylphosphine as promoter, compared to pyridine, this could be readily minimized by including a second promoter, e.g. pyridine.

TABLE I

| Example No. | Promoter* | Conversion, % Nitrobenzene | Selectivity, % Urethane | Selectivity, % Aniline |
|---|---|---|---|---|
| 1 | — | 48 | 48 | 46 |
| 2 | Pyridine | 76 | 90 | 7 |
| 3 | PPh$_3$ | 99 | 75 | 17 |
| 4 | PPh$_3$/Pyridine(1:1) | 98 | 86 | 8 |
| 5 | Et$_4$NBr | 91 | 82 | 10 |
| 6 | Pr$_4$NBr | 96 | 84 | 9 |

*PPh$_3$ = triphenylphosphine
Et$_4$NBr = tetraethylammonium bromide
Pr$_4$NBr = tetrapropylammonium bromide

EXAMPLES 7-9

The procedure was the same as that per Example 2, except that 5.0 ml (90 mmol) of various other alcohols than ethanol were used. The results are shown in table II. It will be noted that higher yields were obtained with the use of the higher carbon number alcohols.

TABLE II

| Example No. | Alcohols | Conversion, % Nitrobenzene | Selectivity, % Urethane | Selectivity, % Aniline |
|---|---|---|---|---|
| 7 | Methanol | 80 | 64 | — |
| 8 | Isopropanol | 82 | 93 | — |
| 9 | Pentanol | 81 | 72 | 1.9 |

EXAMPLE 10

The procedure was the same as that per Example 2, except that 500 psig carbon monoxide was employed. The conversion of nitrobenzene was 32%, but with 89% selectivity to phenyl urethane based on nitrobenzene.

Oxidative Carbonylation Process

EXAMPLES 11-13

A mixture containing 0.47 g (5.0 mmol) aniline, 3.0 ml (52 mmol) ethanol, 2.0 ml benzene as solvent and 1.0 mmol of the various copper catalysts as listed in table III below, but without any promoter, were introduced into a 125 ml autoclave, and 970 psig carbon monoxide and 30 psig oxygen were forced in at room temperature. The mixture was then heated to 150° C. and stirred for 2 hours. After cooling to room temperature, the autoclave was vented and flushed with nitrogen. The mixture was discharged, filtered and analyzed by gas chromatography.

The results are shown in table III, the selectivity indicated being based on aniline.

TABLE III

| Example No. | Copper Catalyst | Conversion, % Aniline | Selectivity, % Urethane |
|---|---|---|---|
| 11 | CuCl$_2$.H$_2$O | 88 | 99 |
| 12 | Cu powder | 69 | 93 |
| 13 | Cu(OAc)$_2$.H$_2$O* | 65 | 25 |

*Cu(OAc)$_2$.H$_2$O = copper acetate

EXAMPLE 14

The procedure was the same as that per Example 12, except that 2.0 mmol potassium iodide were employed as promoter. The conversion of aniline was thereby raised to 98% with 97% selectivity to urethane.

EXAMPLE 15

The procedure was the same as that per Example 12, except that 0.5 mmol copper powder was used, and 1.0 mmol potassium iodide was employed as promoter. The conversion of aniline was 98% with 96% selectivity to urethane.

EXAMPLE 16

The procedure was the same as that per Example 11, except that 4.0 ml (52 mmol) isopropanol were employed, but without a promoter. The conversion of aniline was 63% with 37% selectivity to urethane.

EXAMPLE 17

The procedure was the same as that per Example 14, except that 770 psig carbon monoxide and 30 psig oxygen were employed. The conversion of aniline was 46% with 22% selectivity to urethane, demonstrating that increased pressure generally leads to increased yields.

What is claimed is:

1. A process for producing urethanes, which comprises reacting an organic hydroxyl group containing compound from the group consisting essentially of compounds having at least one aliphatic alcoholically bound hydroxyl group and having 1-20 carbon atoms, and compounds having at least one phenolically bound hydroxyl group and having 6-20 carbon atoms, and carbon monoxide, with an organic nitro group containing compound in the presence of a non-noble metal catalyst system consisting essentially of a copper catalyst.

2. Process of claim 1 wherein the hydroxy group containing compound and carbon monoxide are reacted with an organic nitro group containing compound, and the non-noble metal catalyst system consisting essentially of a mixture of a copper catalyst and a nitrogen or phosphorous containing organic compound as promoter.

3. Process of claim 1 wherein the non-noble metal catalyst system is a copper catalyst from the group consisting essentially of copper powder, copper halide, copper acetate or copper nitrate.

4. Process of claim 2 wherein the copper catalyst is copper powder, copper halide, copper acetate or copper nitrate, and the promoter is tertiary amine, quaternary ammonium salt or tertiary phosphine.

5. Process of claim 1 wherein about 0.05-0.4 mole copper catalyst is used per mole of the nitro group containing compound.

6. Process of claim 2 wherein about 0.05-0.4 mole copper catalyst and about 0.01-10 moles promoter are used per mole of the nitro group containing compound.

7. Process of claim 1 wherein the nitro group containing compound contains at least one nitro group and has 1-20 carbon atoms.

8. Process of claim 1 wherein about 2-500 moles carbon monoxide are used per mole of the nitro group containing compound.

9. Process of claim 1 wherein the reaction is carried out at a pressure of about 200-8000 psig and at a temperature of about 100°-300° C.

10. Process of claim 1 wherein the reaction is carried out in the presence of an inert organic solvent.

11. A process for producing urethanes, which comprises reacting an organic hydroxyl group containing compound from the group consisting essentially of compounds having at least one aliphatic alcoholically bound hydroxyl group and having 1-20 carbon atoms, and compounds having at least one phenolically bound hydroxyl group and having 6-20 carbon atoms, and carbon monoxide, with an organic nitro group containing compound which contains at least one nitro group and has 1-20 carbon atoms, in the presence of a non-noble metal catalyst system consisting essentially of a copper catalyst, in which about 2-500 moles carbon monoxide are used per mole of the nitro group containing compound, the reaction being carried out at about 200-8000 psig and at about 100°-300° C.

12. Process of claim 11 wherein the non-noble metal catalyst system is from the group consisting essentially of a copper catalyst which is copper powder, copper halide, copper acetate or copper nitrate, about 0.05-0.4 mole of the copper catalyst being used per mole of the nitro group containing compound.

13. Process of claim 11 wherein the non-noble metal catalyst system comprises a mixture of about 0.05-0.4 mole copper powder, copper halide, copper acetate or copper nitrate, and about 0.01-10 moles tertiary amine, quaternary ammonium salt or tertiary phosphine as promoter.

14. Process of claim 2 wherein the nitro group containing compound contains at least one nitro group and has 1-20 carbon atoms.

* * * * *